(12) United States Patent
Bender et al.

(10) Patent No.: US 7,309,707 B2
(45) Date of Patent: Dec. 18, 2007

(54) CRYSTALLINE MICRONISATE, PROCESS FOR THE MANUFACTURE THEREOF AND USE THEREOF FOR THE PREPARATION OF A MEDICAMENT

(75) Inventors: Helmut Bender, Wiesbaden (DE); Hagen Graebner, Ingelheim (DE); Konrad Schindler, Ingelheim (DE); Michael Trunk, Ingelheim (DE); Michael Walz, Bingen (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/385,175

(22) Filed: Mar. 10, 2003

(65) Prior Publication Data

US 2004/0002510 A1  Jan. 1, 2004

Related U.S. Application Data

(60) Provisional application No. 60/413,129, filed on Sep. 24, 2002.

(30) Foreign Application Priority Data

Mar. 20, 2002  (DE) ............... 102 12 264

(51) Int. Cl.
*C07D 491/00* (2006.01)
(52) U.S. Cl. ....................... 514/291; 546/91
(58) Field of Classification Search ............... 546/91; 514/291
See application file for complete search history.

(56) References Cited

U.S. PATENT DOCUMENTS

| | | | |
|---|---|---|---|
| 4,042,700 A | 8/1977 | Banholzer et al. | |
| 4,608,377 A | 8/1986 | Banholzer et al. | |
| 4,783,534 A | 11/1988 | Banholzer | |
| 5,610,163 A * | 3/1997 | Banholzer et al. | 514/291 |
| 5,654,314 A | 8/1997 | Banholzer et al. | |
| 5,770,738 A | 6/1998 | Banholzer et al. | |
| 5,952,505 A | 9/1999 | Banholzer | |
| 6,433,027 B1 * | 8/2002 | Bozung et al. | 514/291 |
| 6,455,524 B1 * | 9/2002 | Bozung et al. | 514/229.5 |
| 6,482,429 B1 | 11/2002 | Etzler | |
| 6,486,321 B2 | 11/2002 | Banholzer et al. | |
| 6,506,900 B1 | 1/2003 | Banholzer et al. | |
| 6,585,959 B2 * | 7/2003 | Walz et al. | 424/46 |
| 6,608,054 B2 * | 8/2003 | Meade et al. | 514/229.5 |
| 6,608,055 B2 | 8/2003 | Sieger et al. | |
| 6,620,438 B2 * | 9/2003 | Pairet et al. | 424/489 |
| 6,696,042 B2 * | 2/2004 | Pairet et al. | 424/45 |
| 6,777,423 B2 * | 8/2004 | Banholzer et al. | 514/291 |
| 6,908,928 B2 | 6/2005 | Banholzer et al. | |
| RE38,912 E | 12/2005 | Walz et al. | |
| 7,070,800 B2 | 7/2006 | Bechtold-Peters et al. | |
| 2002/0122773 A1 * | 9/2002 | Pairet et al. | 424/45 |
| 2002/0151541 A1 * | 10/2002 | Pairet et al. | 514/217.05 |
| 2002/0169321 A1 * | 11/2002 | Banholzer et al. | 546/91 |
| 2002/0193392 A1 * | 12/2002 | Schmelzer et al. | 514/291 |
| 2002/0193393 A1 * | 12/2002 | Pairet et al. | 514/291 |
| 2003/0185766 A1 | 10/2003 | Schmelzer | |
| 2003/0235538 A1 * | 12/2003 | Zierenberg | 424/46 |
| 2004/0018153 A1 | 1/2004 | Schmelzer | |

FOREIGN PATENT DOCUMENTS

| | | |
|---|---|---|
| FR | 2 779 347 | 12/1999 |
| WO | WO92/18110 | 10/1992 |
| WO | WO95/05805 | 3/1995 |

OTHER PUBLICATIONS

U.S. Appl. No. 09/961,822, filed Sep. 24, 2001, Banholzer et al.
U.S. Appl. No. 10/354,521, filed Jan. 30, 2003, Banholzer et al.

* cited by examiner

*Primary Examiner*—Zinna N. Davis
(74) *Attorney, Agent, or Firm*—Michael P. Morris; Mary-Ellen M. Devlin; Wendy Petka

(57) ABSTRACT

The invention relates to a crystalline micronisate of (1α,2β, 4β,5α,7β)-7-[(hydroxydi-2-thienylacetyl)oxy]-9,9-dimethyl-3-oxa-9-azoniatricyclo[3.3.1.0$^{2,4}$]nonane-bromide, processes for preparing it and its use for preparing a pharmaceutical composition, particularly for preparing a pharmaceutical composition with an anticholinergic activity.

9 Claims, No Drawings

CRYSTALLINE MICRONISATE, PROCESS FOR THE MANUFACTURE THEREOF AND USE THEREOF FOR THE PREPARATION OF A MEDICAMENT

The invention relates to a crystalline micronisate of (1α,2β,4β,5α,7β)-7-[(hydroxydi-2-thienylacetyl)oxy]-9,9-dimethyl-3-oxa-9-azoniatricyclo[3.3.1.0$^{2,4}$]nonane-bromide, processes for preparing it and its use for preparing a pharmaceutical composition, particularly for preparing a pharmaceutical composition with an anticholinergic activity.

BACKGROUND OF THE INVENTION

The compound (1α,2β,4β,5α,7β)-7-[(hydroxydi-2-thienylacetyl)oxy]-9,9-dimethyl-3-oxa-9-azoniatricyclo [3.3.1.0$^{2,4}$]nonane-bromide, is known from European Patent Application EP 418 716 A1 and has the following chemical structure:

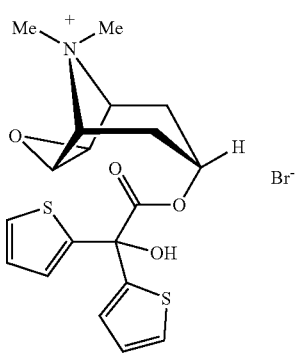

(I)

The compound has valuable pharmacological properties and is known by the name tiotropium bromide (BA679). Tiotropium bromide is a highly effective anticholinergic and can therefore provide therapeutic benefit in the treatment of asthma or COPD (chronic obstructive pulmonary disease).

Tiotropium bromide is preferably administered by inhalation. Suitable inhalable powders packed into appropriate capsules and administered by suitable powder inhalers may be used. Alternatively, it may be administered by the use of suitable inhalable aerosols. These also include powdered inhalable aerosols which contain, for example, HFA134a, HFA227 or mixtures thereof as propellant gas.

In view of the administration of tiotropium bromide by inhalation it is necessary to provide the active substance in a finely divided (or micronised) form. Preferably, the active substance has an average particles size of 0.5 to 10 μm, preferably from 1 to 6 μm, most preferably from 1.5 to 5 μm.

The above particles sizes are generally achieved by grinding (so-called micronisation) of the active substance. As breakdown of the pharmaceutically active substance must be prevented as far as possible as a side-effect of the micronisation, in spite of the hard conditions required for the process, high stability of the active substance during the grinding process is absolutely essential. It should be borne in mind that in some cases, during the grinding process, changes may occur to the solid properties of the active substance, which may influence the pharmacological properties of the formulation which is to be inhaled.

Methods of micronising pharmaceutically active substances are known as such in the prior art. The aim of the present invention is to provide a method which makes micronised tiotropium bromide available in a form which satisfies the stringent requirements imposed on an active substance intended for inhalation and thus takes account of the specific properties of tiotropium bromide.

DETAILED DESCRIPTION OF THE INVENTION

It has been found that, depending on the choice of conditions which can be used when purifying the crude product obtained after industrial manufacture, tiotropium bromide occurs in various crystalline modifications, so-called polymorphs.

It has also been found that these different modifications can be deliberately produced by selecting the solvents used for the crystallisation as well as by a suitable choice of the process conditions used in the crystallisation process.

For the purposes of the present invention, namely to provide tiotropium bromide in a micronised form suitable for inhalation, it has proved suitable to use the crystalline monohydrate of tiotropium bromide, which can be obtained in crystalline form by choosing specific reaction conditions.

In order to prepare this crystalline monohydrate, it is necessary to take up tiotropium bromide which has been obtained, for example, according to the instructions disclosed in EP 418 716 A1, in water, heat it, purify it with activated charcoal and after removing the activated charcoal slowly crystallise out the tiotropium bromide monohydrate by slow cooling. The method described below is preferably used according to the invention.

In a suitably dimensioned reaction vessel the solvent is mixed with tiotropium bromide, which has been obtained for example according to the method disclosed in EP 418 716 A1.

0.4 to 1.5 kg, preferably 0.6 to 1 kg, most preferably about 0.8 kg of water are used as solvent per mole of tiotropium bromide used. The mixture obtained is heated with stirring, preferably to more than 50° C., most preferably to more than 60° C. The maximum temperature which can be selected will be determined by the boiling point of the solvent used, i.e. water. Preferably the mixture is heated to a range from 80–90° C.

Activated charcoal, dry or moistened with water, is added to this solution. Preferably, 10 to 50 g, more preferably 15 to 35 g, most preferably about 25 g of activated charcoal are put in per mole of tiotropium bromide used. If desired, the activated charcoal is suspended in water before being added to the solution containing the tiotropium bromide. 70 to 200 g, preferably 100 to 160 g, most preferably about 135 g water are used to suspend the activated charcoal, per mole of tiotropium bromide used. If the activated charcoal is suspended in water prior to being added to the solution containing the tiotropium bromide, it is advisable to rinse with the same amount of water.

After the activated charcoal has been added, stirring is continued at constant temperature for between 5 and 60 minutes, preferably between 10 and 30 minutes, most preferably about 15 minutes, and the mixture obtained is filtered to remove the activated charcoal. The filter is then rinsed with water. 140 to 400 g, preferably 200 to 320 g, most preferably about 270 g of water are used for this, per mole of tiotropium bromide used.

The filtrate is then slowly cooled, preferably to a temperature of 20–25° C. The cooling is preferably carried out at a cooling rate of 1 to 10° C. per 10 to 30 minutes, preferably 2 to 8° C. per 10 to 30 minutes, more preferably 3 to 5° C. per 10 to 20 minutes, most preferably 3 to 5° C. roughly per 20 minutes. If desired, the cooling to 20 to 25° C. may be followed by further cooling to below 20° C., most preferably to 10 to 15° C.

Once the filtrate has cooled, it is stirred for between 20 minutes and 3 hours, preferably between 40 minutes and 2 hours, most preferably about one hour, to complete the crystallisation.

The crystals formed are finally isolated by filtering or suction filtering the solvent. If it proves necessary to subject the crystals obtained to another washing step, it is advisable to use water or acetone as the washing solvent. 0.1 to 1.0 l, preferably 0.2 to 0.5 l, most preferably about 0.3 l solvent are used, per mole of tiotropium bromide, to wash the tiotropium bromide monohydrate crystals obtained. If desired the washing step may be repeated.

The product obtained is dried in vacuo or using circulating hot air until a water content of 2.5–4.0% is obtained.

The resulting crystalline tiotropium bromide monohydrate is used in the grinding process (micronisation) described below. This process may be carried out using conventional mills. Preferably, the micronisation is carried out with the exclusion of moisture, more preferably, using a corresponding inert gas such as nitrogen, for example. It has proved particularly preferable to use air jet mills in which the material is comminuted by the impact of the particles on one another and on the walls of the grinding container. According to the invention, nitrogen is preferably used as the grinding gas. The material for grinding is conveyed by the grinding gas under specific pressures (grinding pressure). Within the scope of the present invention, the grinding pressure is usually set to a value between about 2 and 8 bar, preferably between about 3 and 7 bar, most preferably between about 3.5 and 6.5 bar. The material for grinding is fed into the air jet mill by means of the feed gas under specific pressures (feed pressure). Within the scope of the present invention a feed pressure of between about 2 and 8 bar, preferably between about 3 and 7 bar and most preferably between about 3.5 and 6 bar has proved satisfactory. The feed gas used is also preferably an inert gas, most preferably nitrogen again. The material to be ground (crystalline tiotropium bromide monohydrate) may be fed in at a rate of about 5–35 g/min, preferably at about 10–30 g/min.

For example, without restricting the subject of the invention thereto, the following apparatus has proved suitable as a possible embodiment of an air jet mill: a 2-inch Microniser with grinding ring, 0.8 mm bore, made by Messrs Sturtevant Inc., 348 Circuit Street, Hanover, Mass. 02239, USA. Using the apparatus, the grinding process is preferably carried out with the following grinding parameters: grinding pressure: about 4.5–6.5 bar; feed pressure: about 4.5–6.5 bar; supply of grinding material: about 17–21 g/min.

The ground material thus obtained is then further processed under the following specific conditions. The micronisate is exposed to a water vapour at a relative humidity of at least 40% at a temperature of 15–40° C., preferably 20–35° C., most preferably 25–30° C. Preferably, the humidity is set to a value of 50–95% r. h., preferably 60–90% r.h., most preferably 70–80% r.h. By relative humidity (r.h.) is meant, within the scope of the present invention, the quotient of the partial steam pressure and the steam pressure of the water at the temperature in question. Preferably, the micronisate obtained from the grinding process described above is subjected to the chamber conditions mentioned above for a period of at least 6 hours. Preferably, however, the micronisate is subjected to the chamber conditions mentioned above for about 12 to 48 hours, preferably about 18 to 36 hours, more preferably about 20 to 28 hours.

In one aspect the invention relates to tiotropium bromide micronisate which may be obtained by the process described above.

The micronisate of tiotropium bromide obtainable by the above method has a characteristic particle size $X_{50}$ of between 1.0 µm and 3.5 µm, preferably between 1.1 µm and 3.3 µm, most preferably between 1.2 µm and 3.0 µm and $Q_{(5.8)}$ of more than 60%, preferably more than 70%, most preferably more than 80%. The characteristic value $X_{50}$ denotes the median value of the particle size below which 50% of the particles fall, with regard to the distribution by volume of the individual particles. The characteristic value $Q_{(5.8)}$ corresponds to the quantity of particles below 5.8 µm, based on the volume distribution of the particles. The particle sizes were determined within the scope of the present invention by laser diffraction (Fraunhofer diffraction). More detailed information on this subject can be found in the experimental descriptions of the invention.

Also characteristic of the tiotropium micronisate according to the invention which was prepared by the above process are Specific Surface Area values in the range between 2 $m^2/g$ and 5 $m^2/g$, more particularly between 2.5 $m^2/g$ and 4.5 $m^2/g$ and most outstandingly between 3.0 $m^2/g$ and 4.0 $m^2/g$.

Carrying out the process according to the invention leads to the micronisate of tiotropium bromide according to the invention which is characterised by specific enthalpies of solution. These preferably have a value of more than 65 Ws/g, preferably more than 71 Ws/g. Most preferably the heat of solution of the micronisate according to the invention is in excess of 74 Ws/g.

Detailed information on determining the enthalpies of solution can be found in the experimental descriptions of the invention.

The tiotropium bromide micronisate which may be obtained using the above process is further characterised in that the water content of the micronisate is between about 1% and about 4.5%, preferably between about 1.4% and 4.2%, more preferably between about 2.4% and 4.1%. Particularly preferred tiotropium bromide micronisate according to the invention is characterised in that the water content of the micronisate is between about 2.6% and about 4.0%, most preferably between about 2.8% and 3.9%, particularly between about 2.9% and 3.8%.

One aspect of the present invention therefore relates to tiotropium bromide micronisate which has the above characteristics.

Within the scope of the present invention, unless otherwise stated, any reference to tiotropium bromide micronisate is to be taken as a reference to the crystalline micronisate of tiotropium bromide which has the above characteristics and which can be obtained by the method according to the invention as described above (micronisation followed by further treatment in accordance with the parameters described above).

In another aspect the present invention relates to the use of the tiotropium bromide micronisate according to the invention as a pharmaceutical composition in view of the pharmaceutical efficacy of the micronisate according to the invention.

In another aspect the present invention relates to inhalable powders characterised in that they contain tiotropium bromide micronisate according to the invention.

In view of the anticholinergic effects of tiotropium bromide a further aspect of the present invention relates to the use of the tiotropium bromide micronisate according to the invention for preparing a pharmaceutical composition for treating diseases in which the use of an anticholinergic agent may have a therapeutic benefit. It is preferably used for preparing a pharmaceutical composition for treating asthma or COPD.

The tiotropium bromide micronisate which may be obtained by the process according to the invention is exceptionally suitable for the preparation of pharmaceutical formulations. It may be used particularly for preparing inhalable powders.

Accordingly, the present invention relates to inhalable powders containing at least about 0.03%, preferably less than 5%, more preferably less than 3% of the tiotropium bromide micronisate obtainable by the process described above in admixture with a physiologically acceptable excipient, characterised in that the excipient consists of a mixture of coarser excipient with an average particle size of 15 to 80 μm and finer excipient with an average particle size of 1 to 9 μm, the proportion of finer excipient in the total amount of excipient being from 1 to 20%.

The percentages specified are percent by weight.

According to the invention, inhalable powders are preferred which contain about 0.05 to about 1%, preferably about 0.1 to about 0.8%, more preferably about 0.2 to about 0.5% tiotropium bromide micronisate, which may be obtained by the method described above and has the characteristics of the micronisate which may be obtained according to the invention.

The inhalable powders containing the micronisate according to the invention are preferably characterised in that the excipient consists of a mixture of coarser excipient with an average particle size of 17 to 50 μm, more preferably 20 to 30 μm and finer excipient with an average particle size of 2 to 8 μm, more preferably 3 to 7 μm. The average particle size here denotes the 50% value from the volume distribution measured by laser diffraction by the dry dispersion method. Preferred powders for inhalation are those wherein the proportion of finer excipient in the total amount of excipient is from 3 to 15%, more preferably 5 to 10%.

Where the present invention refers to a mixture, this always means a mixture obtained by mixing together components which have previously been clearly defined. Accordingly an excipient mixture of coarser and finer ingredients can only refer to mixtures obtained by mixing a coarser excipient component with a finer one.

The coarser and finer excipient fractions may consist of the same chemical substance or chemically different substances, while inhalable powders in which the coarser excipient fraction and the finer excipient fraction consist of the same chemical compound are preferred.

Examples of physiologically acceptable excipients which may be used to prepare the inhalable powders according to the invention include, for example, monosaccharides (e.g. glucose or arabinose), disaccharides (e.g. lactose, saccharose, maltose or trehalose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose, glucose or trehalose is preferred, preferably lactose or glucose, particularly, but not exclusively, in the form of their hydrates. For the purposes of the invention, lactose is the particularly preferred excipient, while lactose monohydrate is most particularly preferred.

The inhalable powders containing the micronisate according to the invention may for example be administered using inhalers which meter a single dose from a reservoir by means of a measuring chamber (e.g. according to U.S. Pat. No. 4,570,630A) or by other means (e.g. according to DE 36 25 685 A). Preferably, however, the inhalable powders are packed into capsules, which are used in inhalers such as those described in WO 94/28958, for example. If the inhalable powder according to the invention is to be packed into capsules or other packages which provide single doses in accordance with the preferred application mentioned above, it is advisable to fill the capsules with amounts of from 1 to 15 mg, preferably 3 to 10 mg, most preferably from 4 to 6 mg of inhalable powder per capsule.

The inhalable powders containing the tiotropium bromide micronisate according to the invention are characterised by a high degree of homogeneity in terms of the accuracy of measuring a single dose. This is in the range from <8%, preferably <6%, most preferably <4%.

The inhalable powders containing the tiotropium bromide micronisate according to the invention may be obtained by the method described below.

After the starting materials have been weighed out, first of all the excipient mixture is prepared from the defined fractions of coarser excipient and finer excipient. Then the inhalable powders according to the invention are prepared from the excipient mixture and the active substance. If the inhalable powder is to be administered using capsules containing powders in suitable inhalers the preparation of the inhalable powder is followed by the manufacture of the capsules containing the powder.

In the preparation methods described below, the abovementioned components are used in the proportions by weight described in the abovementioned compositions of the inhalable powders according to the invention. The inhalable powders according to the invention are prepared by mixing the coarser excipient fractions with the finer excipient fractions and then mixing the resulting excipient mixture with the active substance. To prepare the excipient mixture the coarser and finer excipient fractions are placed in a suitable mixing container. The two components are preferably added through a screening granulator with a mesh size of 0.1 to 2 mm, most preferably 0.3 to 1 mm, even more preferably 0.3 to 0.6 mm. Preferably, the coarser excipient is put in first, and then the finer and coarser excipient are added alternately. It is particularly preferred when preparing the excipient mixture to screen in the two components in alternate layers. Preferably, the two components are screened alternately, in 15 to 45, most preferably 20 to 40 layers each. The two excipients may be mixed while the two components are being added. Preferably, however, the two ingredients are not mixed until after they have been screened in layers.

After the preparation of the excipient mixture, this and the active substance, the tiotropium bromide micronisate according to the invention, are placed in a suitable mixing container. The active substance used has an average particle size of 0.5 to 10 μm, preferably 1 to 6 μm, more preferably 1.5 to 5 μm. The two components are preferably added through a screening granulator with a mesh size of 0.1 to 2 mm, most preferably 0.3 to 1 mm, even more preferably 0.3 to 0.6 mm.

Preferably, the excipient mixture is put in and then the active substance is added to the mixing container. Preferably, in this mixing process, the two components are added in batches. In the preparation of the excipient mixture it is particularly preferred to screen in the two components alternately in 25 to 65, preferably 30 to 60 layers each. The operation of mixing the excipient mixture with the active substance may be carried out while the two components are being added.

Preferably, however, the two ingredients are not mixed until after they have been screened in layers.

The powder mixture obtained by if desired by passed through a screening granulator once more or repeatedly and then subjected to another mixing process.

In another aspect the present invention relates to an inhalable powder which contains the tiotropium bromide micronisate according to the invention and may be obtained by the methods described above.

The following detailed experimental descriptions serve to illustrate the present invention more fully without restricting the scope of the invention to the embodiments described by way of example hereinafter.

Experimental Section

A) Preparation of Crystalline Tiotropium Bromide Monohydrate 15.0 kg of tiotropium bromide, which may be prepared by the experimental procedure disclosed in European Patent Application EP 418 716 A1, are added to 25.7 kg of water in a suitable reaction vessel. The mixture is heated to 80–90° C. and stirred at constant temperature until a clear solution is formed. Activated charcoal (0.8 kg), moistened with water, is suspended in 4.4 kg of water, this mixture is added to the solution containing the tiotropium bromide and rinsed with 4.3 kg of water. The mixture thus obtained is stirred for at least 15 min at 80–90° C. and then filtered through a heated filter into an apparatus which has been preheated to an outer temperature of 70° C. The filter is rinsed with 8.6 kg of water. The contents of the apparatus are cooled at 3–5° C. every 20 minutes to a temperature of 20–25° C. The apparatus is further cooled to 10–15° C. using cold water and crystallisation is completed by stirring for at least one hour. The crystals are isolated using a suction drier, the crystal slurry isolated is washed with 9 litres of cold water (10–15° C.) and cold acetone (10–15° C.). The crystals obtained are dried in a nitrogen current at 25° C. over 2 hours.

Yield: 13.4 kg of tiotropium bromide monohydrate (86% of theory)

Characterisation of Crystalline Tiotropium Bromide Monohydrate

The tiotropium bromide monohydrate obtainable using the method described above was investigated by DSC (Differential Scanning Calorimetry). The DSC diagram shows two characteristic signals. The first, relatively broad, endothermic signal between 50–120° C. can be attributed to the dehydration of the tiotropium bromide monohydrate into the anhydrous form. The second, relatively sharp, endothermic peak at 230±5° C. can be put down to the melting of the substance. This data was obtained using a Mettler DSC 821 and evaluated using the Mettler STAR software package. The data was recorded at a heating rate of 10 K/min.

Since the substance melts with decomposition (=incongruent melting process), the melting point observed depends to a great extent on the heating rate. At lower heating rates, the melting/decomposition process is observed at significantly lower temperatures, e.g. at 220±5° C. at a heating rate of 3 K/min. It is also possible that the melting peak may be split. The split is all the more apparent the lower the heating rate in the DSC experiment.

The crystalline tiotropium bromide monohydrate was characterised by IR spectroscopy. The data was obtained using a Nicolet FTIR spectrometer and evaluated with the Nicolet OMNIC software package, version 3.1. The measurement was carried out with 2.5 µmol of tiotropium bromide monohydrate in 300 mg of KBr. Table 1 shows some of the essential bands of the IR spectrum.

TABLE 1

Attribution of specific bands

| Wave number (cm$^{-1}$) | Attribution | Type of oscillation |
|---|---|---|
| 3570, 3410 | O—H | elongated oscillation |
| 3105 | Aryl C—H | elongated oscillation |
| 1730 | C=O | elongated oscillation |
| 1260 | Epoxide C—O | elongated oscillation |
| 1035 | Ester C—OC | elongated oscillation |
| 720 | Thiophene | cyclic oscillation |

The crystalline tiotropium bromide monohydrate was characterised by X-ray structural analysis. The measurements of X-ray diffraction intensity were carried out on an AFC7R-4-circuit diffractometer (Rigaku) using monochromatic copper $K_\alpha$ radiation. The structural resolution and refinement of the crystal structure were obtained by direct methods (SHELXS86 Program) and FMLQ-refinement (TeXsan Program). Experimental details of the crystalline structure, structural resolution and refinement are collected in Table 2.

TABLE 2

Experimental data on the analysis of the crystalline structure of tiotropium bromide monohydrate.

A. Crystal data

| | |
|---|---|
| Empirical formula | [C$_{19}$H$_{22}$NO$_4$S$_2$] Br.H$_2$O |
| Weight of formula | 472.43 + 18.00 |
| colour and shape of crystals | colourless, prismatic |
| dimensions of crystals | 0.2 × 0.3 × 0.3 mm |
| crystal system | monoclinic |
| lattice type | primitive |
| space group | P 2$_1$/n |
| lattice constants | a = 18.0774 Å, |
| | b = 11.9711 Å |
| | c = 9.9321 Å |
| | β = 102.691° |
| | V = 2096.96 Å$^3$ |
| formula units per elementary cell | 4 |

B. Measurements of intensity

| | |
|---|---|
| Diffractometer | Rigaku AFC7R |
| X-ray generator | Rigaku RU200 |
| wavelength | λ = 1.54178Å (monochromatic copper $K_\alpha$-radiation) |
| current, voltage | 50 kV, 100 mA |
| take-off angle | 6° |
| crystal assembly | steam-saturated capillary |
| crystal-detector gap | 235 mm |
| detector opening | 3.0 mm vertical and horizontal |
| temperature | 18° |
| determining the lattice constants | 25 reflexes (50.8° < 2Θ < 56.2°) |
| Scan Type | ω - 2Θ |
| Scan speed | 8.0 32.0°/min in ω |
| Scan width | (0.58 + 0.30 tan Θ)° |
| 2Θ max | 120° |
| measured | 5193 |
| independent reflexes | 3281 (R$_{int}$ = 0.051) |
| corrections | Lorentz polarisation Absorption (Transmission factors 0.56–1.00) crystal decay 10.47% decay |

TABLE 2-continued

Experimental data on the analysis of the crystalline structure of tiotropium bromide monohydrate.

C. Refinement

| | |
|---|---|
| Reflections (I > 3σI) | 1978 |
| Variable | 254 |
| ratio of reflections/parameters | 7.8 |
| R-values: R, Rw | 0.062, 0.066 |

The X-ray structural analysis carried out showed that crystalline tiotropium bromide hydrate has a simple monoclinic cell with the following dimensions: a=18.0774 Å, b=11.9711 Å, c=9.9321 Å, β=102.691°, V=2096.96 Å$^3$.

The atomic coordinates described in Table 3 were determined by the above X-ray structural analysis:

TABLE 3

| | Coordinates | | | |
|---|---|---|---|---|
| Atom | x | y | z | u (eq) |
| Br(1) | 0.63938(7) | 0.0490(1) | 0.2651(1) | 0.0696(4) |
| S(1) | 0.2807(2) | 0.8774(3) | 0.1219(3) | 0.086(1) |
| S(2) | 0.4555(3) | 0.6370(4) | 0.4214(5) | 0.141(2) |
| O(1) | 0.2185(4) | 0.7372(6) | 0.4365(8) | 0.079(3) |
| O(2) | 0.3162(4) | 0.6363(8) | 0.5349(9) | 0.106(3) |
| O(3) | 0.3188(4) | 0.9012(5) | 0.4097(6) | 0.058(2) |
| O(4) | 0.0416(4) | 0.9429(6) | 0.3390(8) | 0.085(3) |
| O(5) | 0.8185(5) | 0.0004(8) | 0.2629(9) | 0.106(3) |
| N(1) | 0.0111(4) | 0.7607(6) | 0.4752(7) | 0.052(2) |
| C(1) | 0.2895(5) | 0.7107(9) | 0.4632(9) | 0.048(3) |
| C(2) | 0.3330(5) | 0.7876(8) | 0.3826(8) | 0.048(3) |
| C(3) | 0.3004(5) | 0.7672(8) | 0.2296(8) | 0.046(3) |
| C(4) | 0.4173(5) | 0.7650(8) | 0.4148(8) | 0.052(3) |
| C(5) | 0.1635(5) | 0.6746(9) | 0.497(1) | 0.062(3) |
| C(6) | 0.1435(5) | 0.7488(9) | 0.6085(9) | 0.057(3) |
| C(7) | 0.0989(6) | 0.6415(8) | 0.378(1) | 0.059(3) |
| C(8) | 0.0382(5) | 0.7325(9) | 0.3439(9) | 0.056(3) |
| C(9) | 0.0761(6) | 0.840(1) | 0.315(1) | 0.064(3) |
| C(10) | 0.1014(6) | 0.8974(8) | 0.443(1) | 0.060(3) |
| C(11) | 0.0785(5) | 0.8286(8) | 0.5540(9) | 0.053(3) |
| C(12) | −0.0632(6) | 0.826(1) | 0.444(1) | 0.086(4) |
| C(13) | −0.0063(6) | 0.6595(9) | 0.554(1) | 0.062(3) |
| C(14) | 0.4747(4) | 0.8652(9) | 0.430(1) | 0.030(2) |
| C(15) | 0.2839(5) | 0.6644(9) | 0.1629(9) | 0.055(3) |
| C(16) | 0.528(2) | 0.818(2) | 0.445(2) | 0.22(1) |
| C(17) | 0.5445(5) | 0.702(2) | 0.441(1) | 0.144(6) |
| C(18) | 0.2552(6) | 0.684(1) | 0.019(1) | 0.079(4) |
| C(19) | 0.2507(6) | 0.792(1) | −0.016(1) | 0.080(4) |
| H(1) | −0.0767 | 0.8453 | 0.5286 | 0.102 |
| H(2) | −0.0572 | 0.8919 | 0.3949 | 0.102 |
| H(3) | −0.1021 | 0.7810 | 0.3906 | 0.102 |
| H(4) | −0.0210 | 0.6826 | 0.6359 | 0.073 |
| H(5) | −0.0463 | 0.6178 | 0.4982 | 0.073 |
| H(6) | 0.0377 | 0.6134 | 0.5781 | 0.073 |
| H(7) | 0.1300 | 0.7026 | 0.6770 | 0.069 |
| H(8) | 0.1873 | 0.7915 | 0.6490 | 0.069 |
| H(9) | 0.1190 | 0.6284 | 0.2985 | 0.069 |
| H(10) | 0.0762 | 0.5750 | 0.4016 | 0.069 |
| H(11) | 0.1873 | 0.6082 | 0.5393 | 0.073 |
| H(12) | −0.0025 | 0.7116 | 0.2699 | 0.066 |
| H(13) | 0.1084 | 0.8383 | 0.2506 | 0.075 |
| H(14) | 0.1498 | 0.9329 | 0.4626 | 0.071 |
| H(15) | 0.0658 | 0.8734 | 0.6250 | 0.063 |
| H(16) | 0.2906 | 0.5927 | 0.2065 | 0.065 |
| H(17) | 0.2406 | 0.6258 | −0.0469 | 0.094 |
| H(18) | 0.2328 | 0.8191 | −0.1075 | 0.097 |
| H(19) | 0.4649 | 0.9443 | 0.4254 | 0.037 |
| H(20) | 0.5729 | 0.8656 | 0.4660 | 0.268 |
| H(21) | 0.5930 | 0.6651 | 0.4477 | 0.165 |
| H(22) | 0.8192 | −0.0610 | 0.1619 | 0.084 |
| H(23) | 0.7603 | 0.0105 | 0.2412 | 0.084 | x, y, z: fractional coordinates;
U (eq) mean quadratic amplitude of atomic movement in the crystal C) Preparation of the Tiotropium Bromide Micronisate According to the Invention The tiotropium bromide monohydrate obtainable by the process described above is micronised with an air jet mill of the 2-inch microniser type with grinding ring, 0.8 mm bore, made by Messrs Sturtevant Inc., 348 Circuit Street, Hanover, Mass. 02239, USA. Using nitrogen as the grinding gas the following grinding parameters are set, for example:

grinding pressure: 5.5 bar; feed pressure: 5.5 bar; supply (of crystalline monohydrate) or flow speed: 19 g/min.

The ground material obtained is then spread out on sheet metal racks in a layer thickness of about 1 cm and subjected to the following climatic conditions for 24–24.5 hours: temperature: 25–30° C.; relative humidity: 70–80%.

D) Measuring Techniques for Characterizing the Tiotropium Bromide Micronisate According to the Invention The parameters mentioned in the description which characterise the tiotropium bromide micronisate according to the invention were obtained by the measuring techniques and methods described below:

D.1) Determining the Water Content According to Karl-Fischer (Tiotropium Bromide):

| | |
|---|---|
| Titrator | Type Mettler DL 18 with |
| Calibrating substance: | disodium tartrate dihydrate |
| Titrant: | Hydranal-Titrant 5 (Riedel-deHaen) |
| Solvent: | Hydranal Solvent (Riedel-deHaen) |
| | Measuring method: |
| Sample amount: | 50–100 mg |
| Stirring time: | 60 s |

The stirring time before the start of titration ensures that the sample is fully dissolved.

The water content of the sample is calculated by the apparatus in percent and indicated.

D.2) Determining Particle Size by Laser Diffraction (Fraunhofer Diffraction)

Measuring Method:

To determine the particle size the powder is fed into a laser diffraction spectrometer by means of a dispersing unit.

| | |
|---|---|
| Measuring equipment: | Laser diffraction spectrometer (HELOS), Messrs. Sympatec |
| Software: | WINDOX Version 3.3/REL 1 |
| Dispersing unit: | RODOS/Dispersing pressure: 3 bar |
| | Equipment parameters: |
| Detector: | Multielement detector (31 semicircular rings) |
| Method: | Air dispersal |
| Focal length: | 100 mm |
| Measuring range: | RS 0.5/0.9–175 μm |
| Evaluation mode: | HRLD-Mode |
| | Rodos Dry Disperser: |
| Injector: | 4 mm |
| Pressure: | 3 bar |
| Injector vacuum: | maximum (~100 mbar) |
| Suction: | Nilfilsk (advance 5 s) |
| Metering device: | Vibri |
| Feed rate: | 40% (manually increased to 100%) |
| Bed height: | 2 mm |
| Speed of rotation: | 0 |

D.3) Determining the Specific Surface Area (1-Bundle B.E.T. Method):

Measuring Method:

The specific surface is determined by exposing the powder sample to a nitrogen/helium atmosphere at different pressures. Cooling the sample causes the nitrogen molecules to be condensed on the surface of the particles. The quantity of condensed nitrogen is determined by means of the change in the thermal heat conductivity of the nitrogen/helium mixture and the surface of the sample is calculated by means of the surface nitrogen requirement. Using this value and the weight of the sample, the specific surface is calculated.

| Equipment and materials: | |
|---|---|
| Measuring equipment: | Monosorb, Messrs Quantachrome |
| Heater: | Monotektor, Messrs Quantachrome |
| Measuring and drying gas: | nitrogen (5.0)/helium (4.6) 70/30, Messer Griesheim |
| Adsorbate: | 30% nitrogen in helium |
| Coolant: | liquid nitrogen |
| Measuring cell: | with capillary tube, Messrs. W. Pabisch GmbH&Co.KG |
| Calibration peak; | 1000 µl, Fa. Precision Sampling Corp. |
| Analytical scale: | R 160 P, Fa. Satorius |

Calculating the Specific Surface:

The measured values are indicated by the equipment in $[m^2]$ and are usually converted into $[cm^2/g]$ on weighing (dry mass):

$$A_{spez} = \frac{MW * 10000}{m_{tr}}$$

| | |
|---|---|
| $A_{spez}$ = | specific surface $[cm^2/g]$ |
| MW = | Measured value $[m^2]$ |
| $m_{tr}$ = | dry mass [g] |
| 10000 = | conversion factor $[cm^2/m^2]$ |

D.4) Determining the Heat of Solution (Enthalpy of Solution) $E_c$:

The solution enthalpy is determined using a solution calorimeter 2225 Precision Solution Calorimeter made by Messrs. Thermometric.

The heat of solution is calculated by means of the change in temperature occurring (as a result of the dissolving process) and the system-related change in temperature calculated from the base line.

Before and after the ampoule is broken, electrical calibration is carried out with an integrated heating resistor of a precisely known power. A known heat output is delivered to the system over a set period and the jump in temperature is determined.

| Method and equipment parameters: | |
|---|---|
| Solution calorimeter: | 2225 Precision Solution Calorimeter, Messrs Thermometric |
| Reaction cell: | 100 ml |
| Thermistor resistance: | 30.0 kΩ (at 25° C.) |
| Speed of stirrer: | 600 U/min |
| Thermostat: | Thermostat of 2277 Thermal Activity Monitor TAM, Messrs Thermometric |
| Temperature: | 25° C. ± 0.0001° C. (over 24 h) |
| Measuring ampoules: | Crushing ampoules 1 ml, Messrs Thermometric |
| Seal: | Silicon stopper and beeswax, Messrs. Thermometric |
| Weight: | 40 to 50 mg |
| Solvent: | Chemically pure water |
| Volume of solvent: | 100 ml |
| Bath temperature: | 25° C. |
| Temperature resolution: | High |
| Starting temperature: | −40 mK (± 10 mK) temperature-offset |
| Interface: | 2280-002 TAM accessory interface 50 Hz, Messrs Thermometric |
| Software: | SolCal V 1.1 for WINDOWS |
| Evaluation: | Automatic evaluation with Menu point CALCULATION/ANALYSE EXPERIMENT. (Dynamics of base line; calibration after breakage of ampoule). |

Electrical Calibration:

The electrical calibration takes place during the measurement, once before and once after the breakage of the ampoule. The calibration after the breakage of the ampoule is used for the evaluation.

| | |
|---|---|
| Amount of heat: | 2.5 Ws |
| Heating power: | 250 mW |
| Heating time: | 10 s |
| Duration of base lines: | 5 min (before and after heating) |

Evaluation for Tiotropium Bromide Micronisate:

As the mass of the tiotropium bromide micronisate weighed out has to be corrected by the water content of the material, the unsealed ampoules together with about 1 g of the test substance are left to stand open for at least 4 hours. After this equilibration time the ampoules are sealed with the silicon stoppers and the water content of the bulk sample is determined by Karl-Fischer titration. The filled and sealed ampoule is weighed on the scale again. The sample mass is corrected according to the following formula:

$$m_c = \left(\frac{100\% - x}{100\%}\right) \cdot m_w$$

where:

$m_c$ is the corrected mass $m_w$ is the sample mass weighed into the ampoule x is the water content in percent (determined in parallel by Karl-Fischer titration)

The corrected mass $m_c$ determined by this calculation is used as the input value (=weight) to calculate the solution enthalpy measured.

E) Preparation of the Powder Formulation Containing the Tiotropium Bromide Micronisate According to the Invention In the Examples which follow, lactose-monohydrate (200M) is used as the coarser excipient. It may be obtained, for example, from Messrs DMV International, 5460 Veghel/ NL under the product name Pharmatose 200M.

In the Examples which follow, lactose-monohydrate (5μ) is used as the finer excipient. It may be obtained from lactose-monohydrate 200M by conventional methods (micronising). Lactose-monohydrate 200M may be obtained, for example, from Messrs DMV International, 5460 Veghel/ NL under the product name Pharmatose 200M.

Apparatus

The following machines and equipment, for example, may be used to prepare the inhalable powders containing the tiotropium bromide micronisate according to the invention:

Mixing container or powder mixer: Gyrowheel mixer 200 L; type: DFW80N-4; made by: Messrs Engelsmann, D-67059 Ludwigshafen.

Granulating sieve: Quadro Comil; type: 197-S; made by: Messrs Joisten & Kettenbaum, D-51429 Bergisch-Gladbach.

E.1) Preparation of the Excipient Mixture:

31.82 kg of lactose monohydrate for inhalation (200M) are used as the coarser excipient component. 1.68 kg of lactose monohydrate (5 μm) are used as the finer excipient component. In the resulting 33.5 kg of excipient mixture the proportion of the finer excipient component is 5%.

About 0.8 to 1.2 kg of lactose monohydrate for inhalation (200M) are added to a suitable mixing container through a suitable granulating sieve with a mesh size of 0.5 mm. Then alternate layers of lactose monohydrate (5 μm) in batches of about 0.05 to 0.07 kg and lactose monohydrate for inhalation (200M) in batches of 0.8 to 1.2 kg are sieved in. Lactose monohydrate for inhalation (200M) and lactose monohydrate (5 μm) are added in 31 and 30 layers, respectively (tolerance: ±6 layers).

The ingredients sieved in are then mixed together (mixing at 900 rpm).

E.2) Preparation of the Final Mixture

To prepare the final mixture, 32.87 kg of the excipient mixture (1.1) and about 0.13 kg of the tiotropium bromide micronisate according to the invention are used. The content of active substance in the resulting 33.0 kg of inhalable powder is 0.4%.

About 1.1 to 1.7 kg of excipient mixture (E.1) are added to a suitable mixing container through a suitable granulating sieve with a mesh size of 0.5 mm. Then alternate layers of tiotropium bromide micronisate in batches of about 0.003 kg and excipient mixture (E.1) in batches of 0.6 to 0.8 kg are sieved in. The excipient mixture and the active substance are added in 46 and 45 layers, respectively (tolerance: ±9 layers).

The ingredients are sieved and then mixed together.

The final mixture is passed twice more through a granulating sieve and then mixed (mixing at 900 rpm).

E.3) Inhalation Capsules:

Inhalation capsules having the following composition were produced using the mixture obtained according to E.2:

| | |
|---|---|
| tiotropium bromide monohydrate: | 0.0225 mg |
| lactose monohydrate (200 M): | 5.2025 mg |
| lactose monohydrate (5 μm): | 0.2750 mg |
| hard gelatine capsule: | 49.0 mg |
| Total: | 54.5 mg |

Analogously to the method described in E.2 inhalation capsules of the following composition are obtained:

| | | |
|---|---|---|
| a) | tiotropium bromide monohydrate: | 0.0225 mg |
| | lactose monohydrate (200 M): | 4.9275 mg |
| | lactose monohydrate (5 μm): | 0.5500 mg |
| | hard gelatine capsule: | 49.0 mg |
| | Total: | 54.5 mg |
| b) | tiotropium bromide monohydrate: | 0.0225 mg |
| | lactose monohydrate (200 M): | 5.2025 mg |
| | lactose monohydrate (5 μm): | 0.2750 mg |
| | polyethylene capsule: | 100.0 mg |
| | Total: | 105.50 mg |

F) Measuring Techniques for Determining the Particle Sizes of the Excipient Components used in E)

The average particle size of the various excipient ingredients of the formulation containing the tiotropium bromide micronisate according to the invention which may be prepared according to E) was determined as follows:

F.1) Determining the Particle Size of Finely Divided Lactose:

Measuring Equipment and Settings:

The equipment is operated according to the manufacturer's instructions.

| | |
|---|---|
| Measuring equipment: | HELOS Laser-diffraction spectrometer, (SympaTec) |
| Dispersing unit: | RODOS dry disperser with suction funnel, (SympaTec) |
| Sample quantity: | from 100 mg |
| Product feed: | Vibri Vibrating channel, Messrs. Sympatec |
| Frequency of vibrating channel: | 40 rising to 100% |
| Duration of sample feed: | 1 to 15 sec. (in the case of 100 mg) |
| Focal length: | 100 mm (measuring range: 0.9–175 μm) |
| Measuring time: | about 15 s (in the case of 100 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

At least 100 mg of the test substance are weighed onto a piece of card. Using another piece of card all the larger lumps are broken up. The powder is then sprinkled finely over the front half of the vibrating channel (starting about 1 cm from the front edge). After the start of the measurement the frequency of the vibrating channel is varied from about 40% up to 100% (towards the end of the measurement). The time taken to feed in the entire sample is 10 to 15 sec.

F.2) Determining the Particle Size of Lactose 200M:

Measuring Equipment and Settings:

The equipment is operated according to the manufacturer's instructions.

| | |
|---|---|
| Measuring equipment: | Laser diffraction spectrometer (HELOS), Sympatec |
| Dispersing unit: | RODOS dry disperser with suction funnel, Sympatec |

-continued

| | |
|---|---|
| Sample quantity: | 500 mg |
| Product feed: | VIBRI Vibrating channel, Messrs. Sympatec |
| Frequency of vibrating channel: | 18 rising to 100% |
| Focal length (1): | 200 mm (measuring range: 1.8–350 μm) |
| Focal length (2): | 500 mm (measuring range: 4.5–875 μm) |
| Measuring time: | 10 s |
| Cycle time: | 10 ms |
| Start/stop at: | 1% on channel 19 |
| Pressure: | 3 bar |
| Vacuum: | maximum |
| Evaluation method: | HRLD |

Sample Preparation/Product Feed:

About 500 mg of the test substance are weighed onto a piece of card. Using another piece of card all the larger lumps are broken up. The powder is then transferred into the funnel of the vibrating channel. A gap of 1.2 to 1.4 mm is set between the vibrating channel and funnel. After the start of the measurement the amplitude setting of the vibrating channel is increased from 0 to 40% until a continuous flow of product is obtained. Then it is reduced to an amplitude of about 18%. Towards the end of the measurement the amplitude is increased to 100%.

What is claimed is:

1. Crystalline tiotropium bromide micronisate, characterised by a particle size $X_{50}$ of between 1.0 μm and 3.5 μm at a $Q_{(5.8)}$ value of more than 60%, by a specific surface value in the range between 2 m$^2$/g and 5 m$^2$/g, by a specific heat of solution of more than 65 Ws/g and by a water content from about 1% to about 4.5%, wherein the crystalline tiotropium bromide micronisate is obtained from crystalline tiotropium bromide monohydrate, which crystalline tiotropium bromide monohydrate when thermally analysed by DSC has an endothermic maximum at 230±5° C. at a heating rate of 10K/min, has an IR spectrum which has bands inter alia at wavelengths 3570, 3410, 3105, 1730, 1260, 1035 and 720 cm$^{-1}$ and which is characterised by a simple monoclinic cell with the following dimensions: a=18.0774 Å, b=11.9711 Å, c=9.9321 Å, β=102.691°, V=2096.96 Å$^3$.

2. The crystalline tiotropium bromide micronisate according to claim 1, characterised in that the particle size $X_{50}$ has a value of 1.1 μm to 3.3 μm, at a $Q_{(5.8)}$ value of more than 70%.

3. The crystalline tiotropium bromide micronisate according to one of claims 1 or 2, characterised in that it has a specific surface value in the range from 2.5 m$^2$/g to 4.5 m$^2$/g.

4. The crystalline tiotropium bromide micronisate according claim 1, characterised by a specific heat of solution of more than 71 Ws/g.

5. The crystalline tiotropium bromide micronisate according to claim 1, characterised by a water content from about 1.4% to about 4.2%.

6. A process for preparing crystalline tiotropium bromide micronisate which comprises the steps of:
  a) obtaining crystalline tiotropium bromide monohydrate, which crystalline tiotropium bromide monohydrate when thermally analysed by DSC has an endothermic maximum at 230±5° C. at a heating rate of 10K/min, has bands inter alia at wavelengths 3570, 3410, 3105, 1730, 1260, 1035 and 720 cm$^{-1}$ and which is characterised by a simple monoclinic cell with the following dimensions: a=18.0774 Å, b=11.9711 Å, c=9.9321 Å, β=102.691°, V=2096.96 Å$^3$,
  b) micronizing the crystalline tiotropium bromide monohydrate so obtained and,
  c) exposing the resulting micronized crystalline tiotropium bromide at a temperature of about 15 to about 40° C. to water with a relative humidity of at least about 40% for a period of at least about 6 hours.

7. The process according to claim 6, characterised in that the tiotropium bromide monohydrate is micronized under inert gas.

8. The process according to claim 6, characterised in that the tiotropium bromide monohydrate is micronized using an air jet mill with the following grinding parameters:

| | |
|---|---|
| grinding pressure: | about 2–about 8 bar; |
| feed pressure: | about 2–about 8 bar; |
| grinding gas/feed gas: | nitrogen; |
| product supply: | about 5–about 35 g/min. |

9. The process according to claim 8, characterised in that the micronized tiotropium bromide is exposed at a temperature of about 20—about 35° C. is exposed to water vapour at a relative humidity of about 50—about 95% for a period of about 12 to 48 hours.

* * * * *

UNITED STATES PATENT AND TRADEMARK OFFICE
CERTIFICATE OF CORRECTION

PATENT NO. : 7,309,707 B2  Page 1 of 1
APPLICATION NO. : 10/385175
DATED : December 17, 2007
INVENTOR(S) : Helmut Bender et al.

It is certified that error appears in the above-identified patent and that said Letters Patent is hereby corrected as shown below:

In Column 15, Line 30:

"Crystalline tiotropium bromide micronisate, characterized by a particle size X50 of between 1.0 µm and 3.5 µm at a Q(5.8) value of more than 60%,.........."

Should read:

--Crystalline tiotropium bromide micronisate, characterized by a particle size X50 of between 1.0 µm and 3.5 µm, at a Q(5.8) value of more than 60%,..........--

Signed and Sealed this

Thirteenth Day of May, 2008

JON W. DUDAS
*Director of the United States Patent and Trademark Office*

UNITED STATES PATENT AND TRADEMARK OFFICE
CERTIFICATE OF CORRECTION

PATENT NO.         : 7,309,707 B2
APPLICATION NO. : 10/385175
DATED              : December 18, 2007
INVENTOR(S)       : Helmut Bender et al.

It is certified that error appears in the above-identified patent and that said Letters Patent is hereby corrected as shown below:

In Column 15, Line 30:

"Crystalline tiotropium bromide micronisate, characterized by a particle size X50 of between 1.0 µm and 3.5 µm at a Q(5.8) value of more than 60%,.........."

Should read:

--Crystalline tiotropium bromide micronisate, characterized by a particle size X50 of between 1.0 µm and 3.5 µm, at a Q(5.8) value of more than 60%,..........--

This certificate supersedes the Certificate of Correction issued May 13, 2008.

Signed and Sealed this

Seventeenth Day of June, 2008

JON W. DUDAS
*Director of the United States Patent and Trademark Office*